(12) United States Patent
Linder et al.

(10) Patent No.: US 7,473,265 B2
(45) Date of Patent: Jan. 6, 2009

(54) FILTER MEDIA AND METHODS OF MANUFACTURE

(75) Inventors: Richard J. Linder, Sandy, UT (US); Daryl R. Edmiston, Sandy, UT (US); Steven W. Johnson, West Jordan, UT (US); Steven M. Wood, West Jordan, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 516 days.

(21) Appl. No.: 10/800,522

(22) Filed: Mar. 15, 2004

(65) Prior Publication Data

US 2005/0203567 A1    Sep. 15, 2005

(51) Int. Cl.
*A61M 29/00*    (2006.01)
(52) U.S. Cl. ..................................... 606/200
(58) Field of Classification Search ................ 606/200, 606/113, 114, 127, 108, 159, 191–198
See application file for complete search history.

(56) References Cited

U.S. PATENT DOCUMENTS

| | | | |
|---|---|---|---|
| 3,472,230 | A | 10/1969 | Fogarty |
| 3,592,186 | A | 7/1971 | Oster |
| 3,683,904 | A | 8/1972 | Forster |
| 3,889,657 | A | 6/1975 | Baumgarten |
| 3,952,747 | A | 4/1976 | Kimmell, Jr. |
| 3,996,938 | A | 12/1976 | Clark, III |
| 4,046,150 | A | 9/1977 | Schwartz et al. |
| 4,425,908 | A | 1/1984 | Simon |
| 4,447,227 | A | 5/1984 | Kotsanis |
| 4,580,568 | A | 4/1986 | Gianturco |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Kevin T Truong
(74) *Attorney, Agent, or Firm*—Crompton, Seager & Tufte LLC (57) ABSTRACT

Filters and method of manufacturing filters are disclosed herein. The filter has a substantially sack-like shape having a closed distal end and an open proximal end. The filter can be constructed from thin film. The filter material can be an organic or inorganic polymer. In one embodiment, the filter material is a polyurethane film having a thickness of les than 25 μm. The filter can be constructed from one or more sections of filter material. In the two-section embodiment, the outer edges of the first and second sections are overlapped and bonded using solvent, heat or other bonding process. In the single-section embodiment, the outer edges of the first section are overlapped and bonded using bonding agents, such as solvent or adhesive, heat or other bonding process. Filters of the present invention have a reduced amount of hysteresis so as to reform to its original shape when deployed.

18 Claims, 5 Drawing Sheets

U.S. PATENT DOCUMENTS

| | | |
|---|---|---|
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,886,061 A | 12/1989 | Fischelle et al. |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Gifford, III et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,224,953 A | 7/1993 | Morgentaler |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,484 A | 7/1994 | Gunther |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazerus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vowerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren et al. |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,807,398 A | 9/1998 | Shaknovich |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |

| Patent Number | Date | Inventor |
|---|---|---|
| 5,925,016 A | 7/1999 | Chornenky et al. |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,941,869 A | 8/1999 | Patterson et al. |
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler et al. |
| 5,976,172 A | 11/1999 | Homsma et al. |
| 5,980,555 A | 11/1999 | Barbut et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,511,496 B1 * | 1/2003 | Huter et al. ............ 606/200 |
| 6,939,362 B2 * | 9/2005 | Boyle et al. ............ 606/200 |
| 7,163,549 B2 * | 1/2007 | Crank et al. ............ 606/200 |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/04875 A1 | 2/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | EP 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |

| WO | WO 00/16705 | 3/2000 |
| WO | WO 00/49970 | 8/2000 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam, "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

FILTER MEDIA AND METHODS OF MANUFACTURE

BACKGROUND OF THE INVENTION

1. The Field of the Invention

The present invention relates to embolic protection devices. More particularly, the present invention relates to filters and methods of manufacturing the filters.

2. The Relevant Technology

Human blood vessels often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded blood vessels in a patient caused by the deposit of plaque or other material on the walls of the blood vessels. Angioplasty, for example, is a widely known procedure wherein an inflatable balloon is introduced into the occluded region. The balloon is inflated, dilating the occlusion, and thereby increasing the intraluminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the tip thereof. Also located at the tip are an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

In another procedure, stenosis within arteries and other blood vessels is treated by permanently or temporarily introducing a stent into the stenosed region to open the lumen of the vessel. The stent typically includes a substantially cylindrical tube or mesh sleeve made from such materials as stainless steel or nitinol. The design of the material permits the diameter of the stent to be radially expanded, while still providing sufficient rigidity such that the stent maintains its shape once it has been enlarged to a desired size.

Unfortunately, such percutaneous interventional procedures, i.e., angioplasty, atherectomy, and stenting, often dislodge material from the vessel walls. This dislodged material can enter the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, kidneys, or brain, resulting in a stroke or infarction.

Some existing devices and technology use a filter for capturing the dislodged material from the bloodstream. Usually, the filter includes a filter material which includes pores or openings to allow the blood to pass therethrough while at the same time preventing larger debris from passing therethrough. Generally, the filter material is constructed from an organic or inorganic polymer. Suitable polymeric materials can be formed into a thin film using a variety of techniques such as extrusion, dip molding, stretching, casting, and calendering.

Polymer films can be constructed quite thinly, usually having wall thicknesses of about 1 mil (25 μm). However, it would be an advantage to have a polymer film that has an even thinner wall thickness. Having a thinner film or material allows a greater volume of filter material to be packed into a mechanism to deploy the filter. As a result, more filtering media is provided for the filtering function, allowing more debris to be caught by the filtering mechanism.

In addition, a desired characteristic of filter material is that it has a degree of elasticity or some elastomeric attribute. As the fluid is passing through the filter material, it is desirable that the filter material is somewhat elastomeric so that the flow of the bloodstream does not rupture the filter material.

The filter material should also have high tear strength to withstand the fluid flow across the surface area of the filter material. In addition, it is desirable that the filter material have high tensile strength for many of the same reasons that it should have high tear strength and have elasticity.

In order to maintain the desired strength and flexibility of the filter material, it is important that the filter material maintain a consistent thickness. In many types of thin materials, generally as the thickness of the material decreases, these desired qualities of high elasticity, high tear strength and high tensile strength also decreases. Thus, certain processes, such as dip coating, are not suitable for providing filter material with consistent thickness. In the dip coating process, an operator dips a mandrel into polymer which is dissolved in a carrier or solvent. The mandrel is then withdrawn at a certain velocity. Depending on the rate of withdrawal and depending on the viscosity of the fluid, the thickness of the filter material is controlled. However, when the solvent comes off the mandrel, it results in an inconsistent thickness of the filter material. In addition, the dip coating process is limited on how thin the filter material can be formed. Furthermore, the dip molding process at the molecular level results in a very homogeneous molecular structure that actually reduces the tear strength and tensile strength of the resultant filter material.

Where the filter material is a thin film, the thin film requires special handling. As such, manufacturing costs can be quite high due to the delicate and thin nature of the material. However, it would be desirable to make the manufacturing process steps as simple as possible to reduce costs. In addition, it is desirable to make a process which is safe. For example, PTFE (polytetrafluoroethylene) film can be made from extrusion or stretching processes. However, PTFE films are generally difficult to work with, requiring dangerous solvents or heat bonding processes. Furthermore, extrusion or stretching processes still do not produce the desired film thinness or the desired tear strength required for bloodstream filtering applications.

In addition, it is desirable to be able to pack the filter material within some sort of deployment mechanism in order to navigate the filter material through the vascular system of the patient. Once a filter mechanism is positioned at the correct location, the filter material should then be easily deployed such that it closely reforms to its original shape. Various characteristics of the filter material influence its ability to be restored back to its original shape. Such characteristics include compliancy, stiffness, thickness, resiliency, and elastomericity.

Many conventional filter materials do not have adequate compliancy, are too stiff, are too thick, not sufficiently resilient or elastomeric to reform back to the original shape when deployed. Rather, they usually remain partially compressed or end up having many folds or wrinkles on the surface area thereof. However, such folds and wrinkles produces what is known as hysteresis. Existence of hysteresis in the filter material has a potential to weaken, or even rupture or tear the filter material at the location of the fold or wrinkle. Additionally, folded areas may not be fully exposed to the blood flow so as to decrease the efficiency of the filtering. Thus, it is advantageous to reduce the amount of hysteresis in the deployed filter media.

BRIEF SUMMARY OF THE INVENTION

The present invention is directed to filters and methods and apparatuses for constructing such filters. The filters of the present invention can be used in embolic protection devices configured to filter embolic debris from the bloodstream of a patient. In one embodiment, the embolic protection device includes a filter assembly located at a distal end thereof. The filter assembly includes a filter and a filter basket. The filter basket includes one or more struts which are biased to open outwardly. The filter is a generally sack-like structure which includes a closed distal end and an open proximal end. As such, portions of the proximal end are connected to the ends of the struts. When the struts move outwardly, this in turn opens the filter to the flow of the bloodstream.

As discussed above, the filter is generally a sack-like shape having a distal end and a proximal end. The sack-like filter can have any suitable sack-like shape. In one configuration, the sack-like shape has a substantially conical shape. The distal end is generally closed, although can have structures (e.g. a guide-wire tip) extending therethrough. In contrast, the proximal end of the filter is open ended. The filter can have one or more seams extending between the proximal end and the distal end of the filter. For instance, a seam can be formed as two edges of filter material are bonded together, whether or not such edges are associated with a single piece of filter material, i.e., opposite edges of a single piece of filter material, or two or more pieces of filter material, i.e., one edge from a first piece of filter material and another edge from a second piece of filter material.

Characteristics which can be desired of the filter material include, but are not limited to, that it is extremely thin, has a degree of elasticity, has high tensile strength, and has high tear strength. In addition, it is generally desired that the filter material has substantially consistent thickness throughout the surface area thereof. Further, it can be desirable for the filter material to have an adequate degree of compliancy so that the filter can easily reform back to its pre-packed shape when deployed in the blood vessel. The filter material should generally exhibit a reduced amount of hysteresis when being deployed. Moreover, it is desirable that the filter material be biocompatible and any bonding processes be biocompatible.

In one configuration, the filter material is constructed of one or more thin pieces of material. For example, the filter material can be a thin film having a thickness of less than about 25 μm, less than about 10 μm, or even a thickness of about 5 μm.

In one configuration, the filter material can be a polymer film. The polymer film can be formed using a high pressure roller in order to further thin a sheet of polymer film. The stressing process undergone by the rollers also aligns the polymer strands which increases the strength of the polymer film. Other processes for forming a sufficiently thin film include, but are not limited to, extrusion, stretching, dip molding, blow molding. In one embodiment, a polyurethane film is used having a thickness of less than 25 μm.

The filter can be made from one or more pieces or sections of filter material. In one embodiment, the filter can be constructed from two pieces of filter material. In another embodiment, the filter can be constructed from a single piece of filter material. In addition, in other configurations, the filter can be constructed from more than two pieces of filter material.

The sections of filter material are generally cut out or formed from a larger piece of filter material. The sections can be cut, under computer control, by an Eximer laser. Alternatively, the sections can be formed using a pattern. The pattern, having the configuration or shape desired for the section, can be placed over a section of filter material. Once in place, a wide laser beam is passed over the pattern to burn away all of the filter material outside of the periphery of the pattern to leave behind the shaped piece. Alternatively, a solvent or a chemical capable of etching or removing a portion of the filter material can be used to wash away materials outside the edges of the pattern. Such chemicals, can include, but not limited to, caustic chemicals, acids, mixtures of acids or caustic chemicals, or other chemicals capable of etching or removing a portion of the filter material.

To form a conically shaped sack-like filter, the one or more sections of filter material are each constructed having a substantially tapered configuration. That is, each section of filter material has a proximal end and a distal end with a generally tapering configuration from the proximal end to the distal end. The proximal end can have notched or serrated configurations to assist in connecting the filter to other structures of the filter assembly. Where the section of filter material is generally tapered, the section of filter material will include two generally angled edges which can be planer, curved, or alternatively, have protruding portions. For example, in one configuration, the edges have a generally parallel portion and a generally angular portion. The sections can have various polygonal configurations.

Each section of filter material includes a porous region. The porous region can be formed a distance from the outer periphery of the section or can cover the entire surface of the section. The porous regions can be formed during manufacturing of the sections. Alternatively, the porous regions can be formed during the formation of the filter material itself. The pores can have various configurations including, but not limited to, circular, oval, polygonal, and the like. The diameter of the pores can range from about 50 μm to about 200 μm.

A clamping assembly can be used to hold together adjacent or overlapping edges of the section(s) of filter material and to protect the rest of the section from the selected bonding process. In one configuration, where two sections of filter material are used to form the sack-like filter, a clamping assembly is provided having a first die portion and a second die portion. The first die portion provides a first clamping surface and the second die portion provides a second clamping surface. In one configuration, the clamping surfaces are shaped substantially similar to the shape of the pieces of filter material. In one embodiment, the surface area of the sections of filter material is slightly larger than the surface area of the clamping surfaces so that a portion of the filter material is exposed outside the periphery of the die portions. The clamping assembly is selectively positionable between an open and closed position. Alignment means can be provided to align the die portions.

In one embodiment, the outer edge of one or both clamping surfaces includes a slightly chamfered edge. This increases the size of the portion of the sections of filter material that can be exposed to the bonding process. Where both clamping surfaces have a chamfered edge, it also creates a groove which holds a bonding agent so that the bonding agent has sufficient space and time to bond the adjacent edges of the filter material together. In addition, the groove forms a guide for an operator to apply a removing tool to remove portions of the bonding agent and filter material outside and/or within the groove to complete the bonding process.

The clamping assembly can be constructed from metal, ceramic, plastic or other material which provides a high enough clamping force and is resistant to the selected bonding process. In addition, the material is preferably reasonably corrosion resistant.

The process for bonding two sections of filter material can include placing the sections of filter material horizontally on the first clamping surface. A second clamping surface is placed over the overlapped sections. At least a portion of the first edge of the first section overlaps at least a portion of the first edge of the second section. Similarly, at least a portion of the second edge of the first section overlaps at least a portion of the second edge of the second section. The clamping surfaces are then placed in the closed position. In one configuration, at least a portion of the edges are exposed outside of the clamping assembly. The edges can then be bonded using a bonding agent, such as solvent or adhesive, heat, or other bonding process, or a combination thereof to form the sack-like filter. A tool can be optionally applied to the groove formed by the chamfered edges to remove excess bonding agent and/or the discarded portions of the edges of the sections of filter material.

In yet another configuration, the sack-like filter can be formed from a single section of filter material. The single section of filter material can be substantially tapered having a first edge, second edge, and a third edge. The filter material also has a porous region. The first edge and second edge are configured to be bonded together to form the substantially conical shaped sack-like filter. A clamping assembly can be provided having, instead of clamping surfaces, a first blade and a second blade. The first edge and second edge are overlapped and the blades placed over the overlapping edges to provide a high clamping force thereon. The blades can include chamfered edges similar to the clamping surfaces. The first edge and second edge can then be bonded using a bonding agent, heat, or other bonding process, or a combination thereof to form the sack-like filter. Advantageously, the filter formed of a single piece of filter material results in only one seam, thus minimizing the number of weak points in the filter.

These and other objects and features of the present invention will become more fully apparent from the following description and appended claims, or can be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE EXEMPLARY EMBODIMENTS

Figure 1:
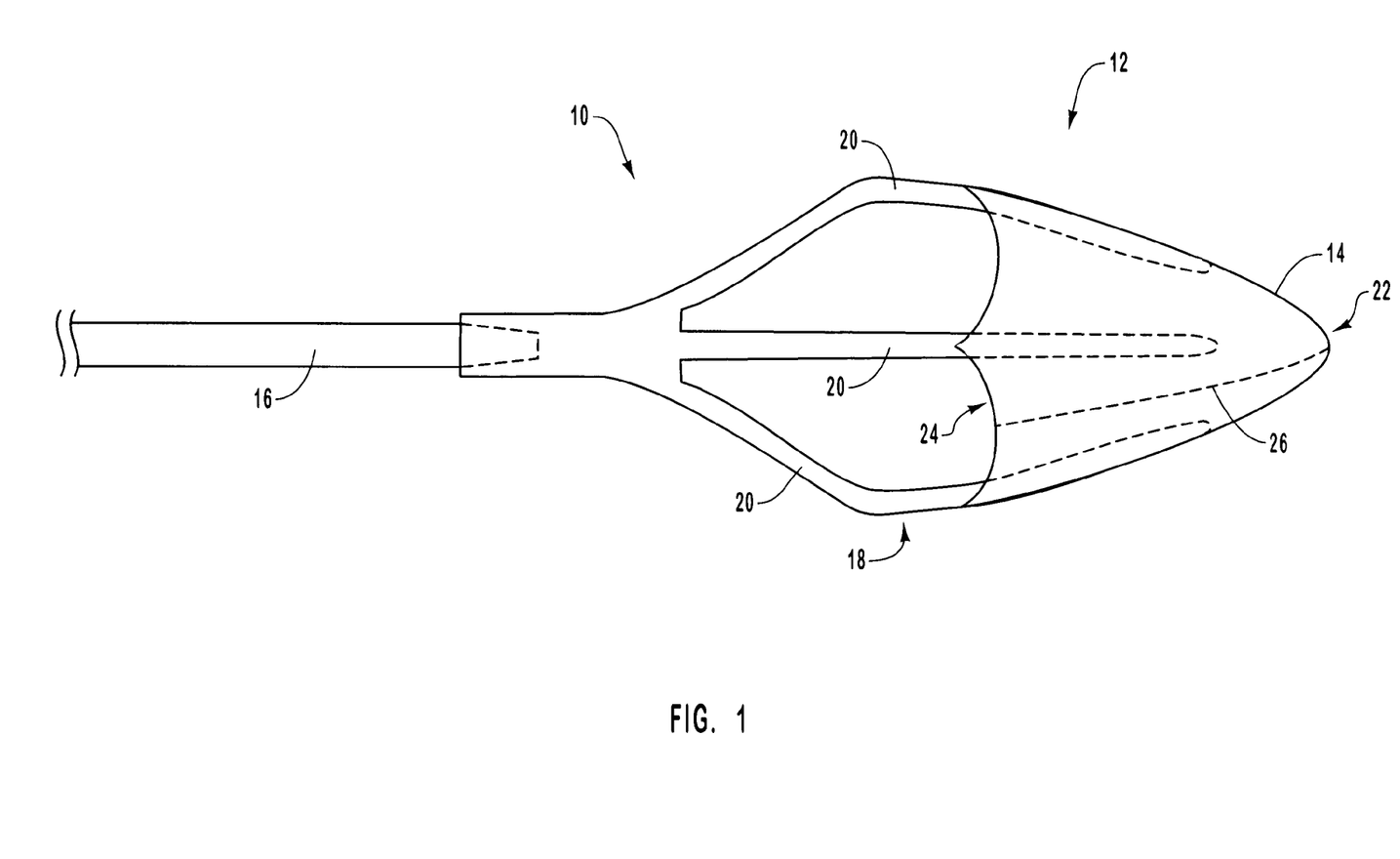
FIG. 1 illustrates a side view of the distal end of an embolic protection device, showing a filter assembly with a filter constructed according to one exemplary embodiment of the present invention, where the filter assembly is in a deployed position.

With reference to FIG. 1, a portion of an embolic protection device 10 is shown that uses a filter 14 of the present invention. General features of the embolic protection device 10 will be discussed herein, but it will be understood that the filter 14 of the present invention can be used with various other configurations of the embolic protection device.

The embolic protection device 10 uses the filter 14 to filter the blood flowing therethrough and prevent large pieces of debris from moving downstream of a surgical site. To aid with this, the embolic protection device 10 includes a filter assembly 12 located at a distal end of the embolic protection device 10. The filter assembly 12 attaches to a distal end of a guide member 16 that aids with positioning the filter assembly 12 within the vasculature of a patient. The guide member 16 can have various configurations, so long as it has sufficient torqueability, rigidity, and flexibility to move through the tortuous anatomy of a patient. In one configuration, the guide member 16 is a metallic member, while in other configurations the guide member 16 can be composite materials, alloys, or other materials.

The filter assembly 12 includes the filter 14 and a filter basket 18 to support the filter 14. More specifically, the filter basket 18 includes a proximal end that attaches to a distal end of the guide member 16, while integrally formed with or attached to a distal end of the filter basket 18 are one or more struts 20. These struts 20, move outwardly to deploy the filter 14 during use of the embolic protection device 10. Further details regarding the struts 20, the filter basket 18 and generally the embolic protection device 10 can be found in co-pending U.S. patent application Ser. No. 10/186,275, filed Jun. 28, 2002, entitled "Methods, systems and devices for providing embolic protection and removing embolic material" and U.S. patent application Ser. No. 10/290,099, filed Nov. 7, 2002 and entitled "Methods, systems and devices for delivering stents,", the disclosures of which applications are incorporated herein by reference.

With continued reference to FIG. 1, the filter 14 has a sack-like shape. In particular, the filter 14 has a distal end 22 and a proximal end 24. The distal end 22 of the filter 14 is illustrated as being closed. In contrast, the proximal end 24 of the filter 14 is open-ended. The cross section of the filter 14 is configured to substantially span the cross section of a blood vessel (not shown) in which the filter 14 is located. As such, substantially all of the fluid flowing through the blood vessel comes in contact with a portion of the filter 14. In this manner, the filter 14 is configured to filter embolic debris from a dynamic stream of blood.

As shown in FIG. 1, the filter 14 can have one or more seams 26 which result from the bonding of two portions of the filter material forming the filter 14, such that the filter 14 has a sack-like shape. The seams 26, only one being shown in FIG. 1, generally extend between the distal end 22 and the proximal end 24 of the filter 14. For instance, the seam 26 can be formed as two edges of filter material are bonded together, whether or not such edges are associated with a single piece of filter material, i.e., opposite edges of a single piece of filter material, or two or more pieces of filter material, i.e., one edge from a first piece of filter material and another edge from a second piece of filter material. The manufacture of the filter 14 will be discussed in further detail below.

The filter material of the filter 14 can be extremely thin, have a high degree of elasticity, have high tensile strength, and have high tear strength. In addition, the filter material can have a substantially consistent thickness throughout the surface area thereof so as to maximize the strength of the filter material and prevent weak spots. In other configurations, the filter material can have irregular or non-uniform thickness. In this latter configuration, increased filter strength can be created by increasing the thickness of the filter material. For instance, additional strength can be desired at locations where the struts 20 attached to the filter 14. Similarly, the distal end 22 can have a thickness greater than other portions of the filter material to limit the potential for tearing during capturing of embolic material or during removal of the embolic protection device 10.

As discussed earlier, the filter assembly 12 and associated filter 14 are usually tightly packed in some fashion before being deployed in the blood vessel. Suitable filter materials for the filter 14 have an adequate degree of compliancy so that the filter 14 can easily reform back into its pre-packed shape when deployed in the blood vessel. Furthermore, it is desirable that when the filter 14 is deployed, there is a reduced amount of hysteresis that is found, when compared with conventional filters. Hysteresis refers to the folds and/or wrinkles that are created by tightly packing the filter material of the filter 14.

Generally, the filter material for the filter 14 can be, but not limited to, organic or inorganic polymers. Organic polymers include, but are not limited to, density polyethylene (LDPE), polyethylene terphthalate (PET), polytetrafluoroethylene (PTFE), fluorinated ethylene propylene (FEP), polyethylene (PE), polyurethane (PU), polycarbonate (PC), polyvinylchloride (PVC), or combinations thereof. Alternatively, the filter material can be fabricated from one or more metals, alloys, synthetics, composites, or other materials having the desired medical characteristics and that are capable of being formed as a thin film.

In one configuration, the filter material for the filter 14 is constructed of one or more thin pieces of material. For example, the filter material can be a thin film having a thickness of less than about 25 µm (1 mil), less than about 10 µm, or even a thickness of about 5 µm. For the case of using a thin film for the filter 14, a suitable thin film is selected such that manipulation of the thin film into a sack-like structure is easily facilitated. That is, when working with such thin films, it is desirable to provide processes that are easily implemented manually. Furthermore, because the filter 14 is intended to be placed within a human body or other organism, it is desirable that the filter material itself be biocompatible and any seams formed on the edges of the thin film are formed using biocompatible bonding agents and/or safe heat processes. It can be understood that the filter material can be fabricated from a mesh or a thin film having a plurality of pores or holes therethrough.

The filter material forming the filter 14 can be, in one configuration, a polymer film. In one exemplary configuration, the polymer film can be formed from a rolling process. One exemplary process can be, but not limited to, a calendaring process where one or more rollers roller the film as one or more of the rollers move in one direction and one or more of the rollers move in the opposite direction. Other processes are known and generally any process for creating the thin film is possible.

In this exemplary configuration, the process uses one or more high pressure roller to further press one or more layers of polymer film in order to make the polymer film even thinner. This stressing process undergone by the rollers also has the effect of aligning the polymer strands so as to increase the strength of the polymer film. In fact, the tear strength can actually be increased by this aligning process despite the fact that the polymer film is becoming even thinner. One exemplary polymeric material for applying this thinning process is polyurethane. However, other polymeric materials can be suitable including, but not limited to, those identified above. In addition, other processes can be suitable for forming a thin film or the filter material of the filter. These other processes can include, but are not limited to, extrusion, stretching, pressing, rolling, blow molding, or other processes that can create the desired filter material.

In one configuration, polyurethane films are used because they are biocompatible, can be formed into a sack-like structure using biocompatible methods, provides the desired elasticity, tensile strength and tear strength, and also contains sufficient compliancy so that it reforms substantially back to its original shape with a minimal amount of hysteresis.

With respect to FIG. 1, the filter 14 has pores formed therein so as to catch the debris flowing in the blood stream. While the embodiments and configurations of the present invention show that the filter 14 has a substantially conical shape, the filter 14 can be configured into any suitable sack-like shape using the systems and methods taught herein. One advantage of a conically shaped filter is that as the longitudinal axis oz of the cone is lengthened, the surface area of the filter increases, thus increasing the amount of surface area available for filtration.

Figure 2A:
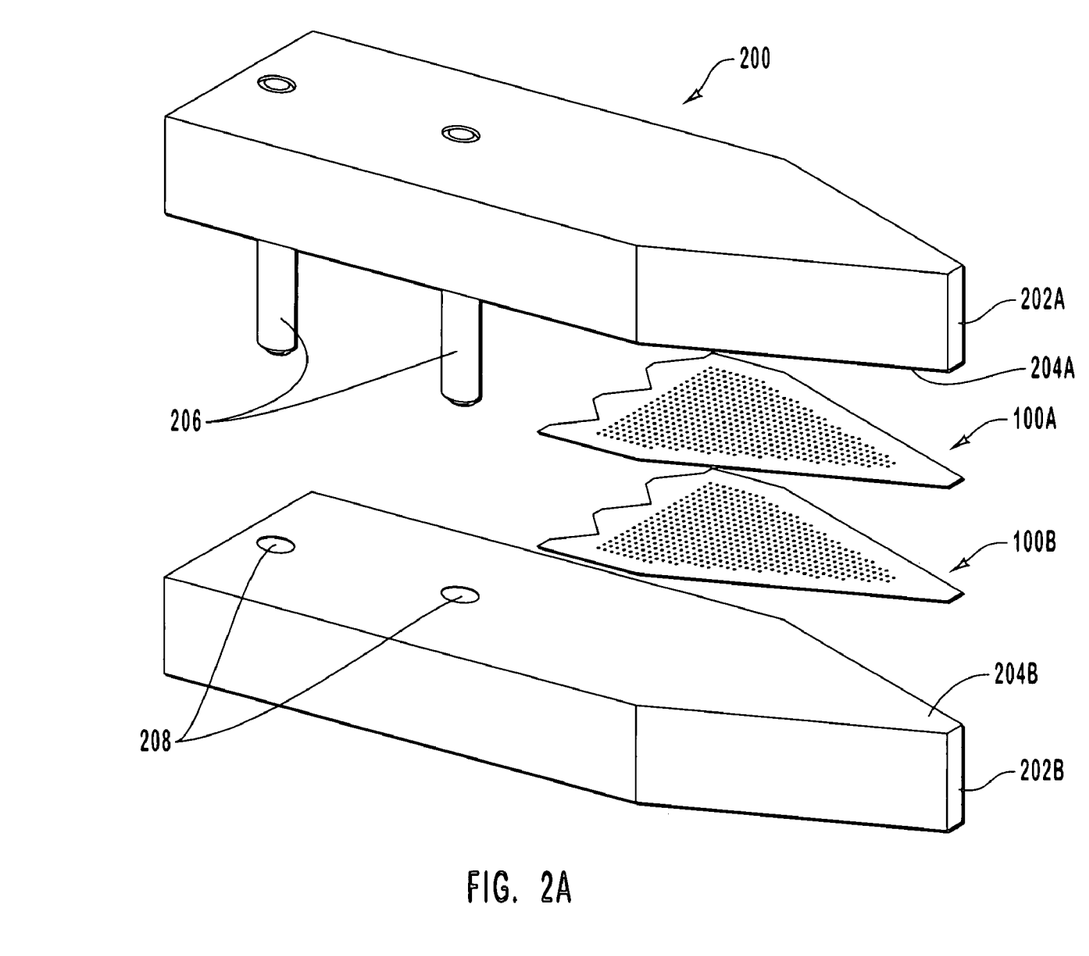
FIG. 2A illustrates a clamping assembly for assembling the filter of FIG. 1.
Figure 2B:
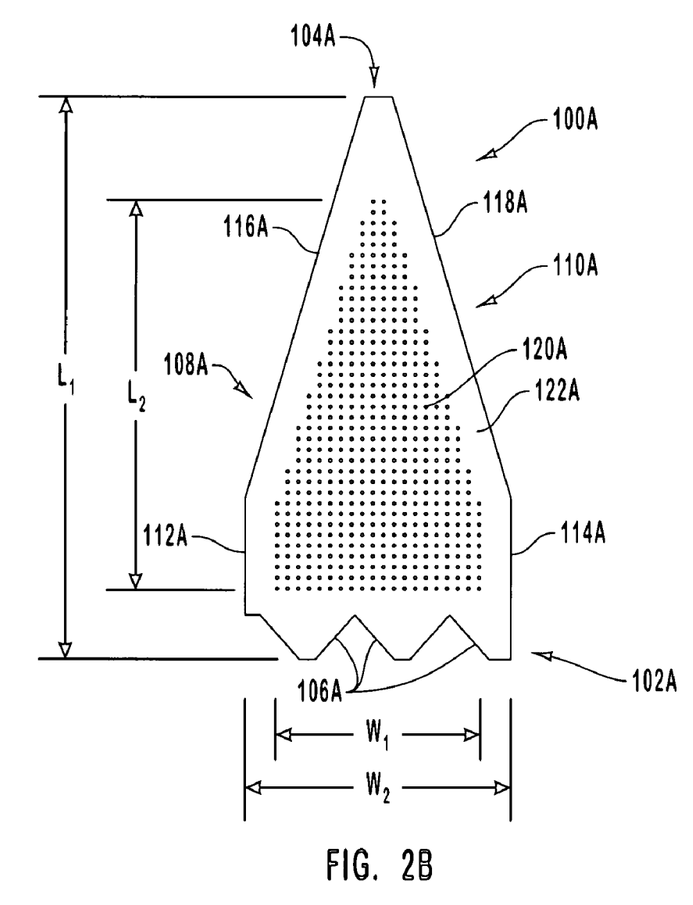
FIG. 2B illustrates one of the sections of the filter material of FIG. 2A.
Figure 2C:
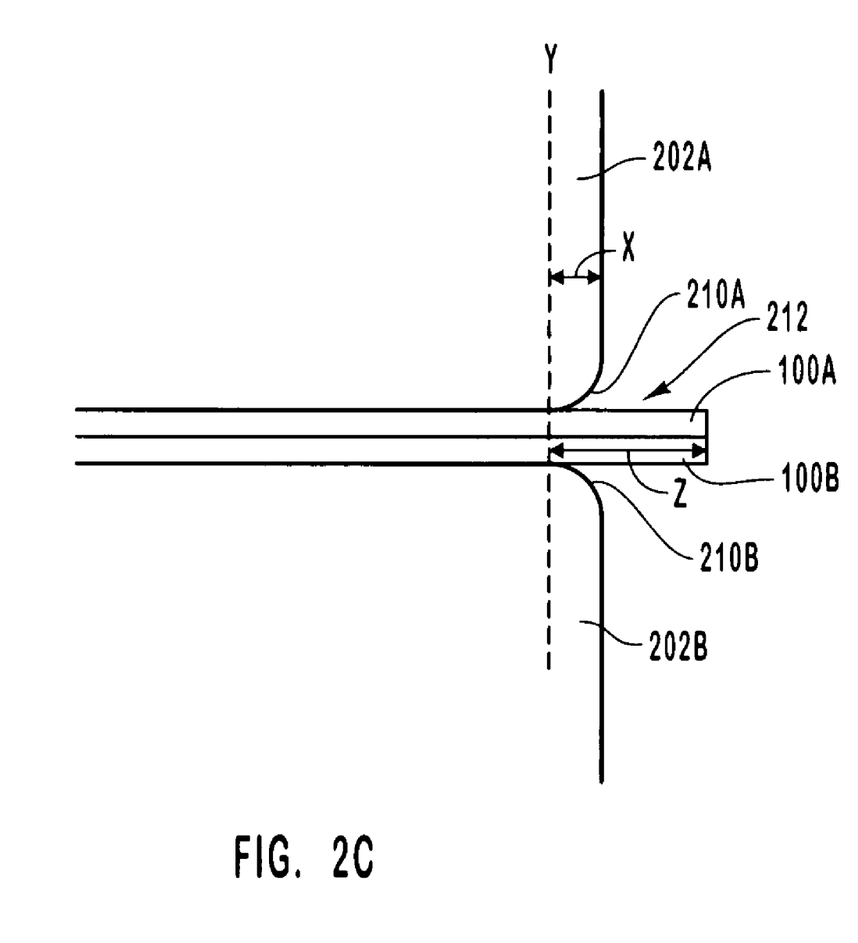
FIG. 2C illustrates a partial side view of the clamping assembly of FIG. 2A in the closed position.
Figure 3A:
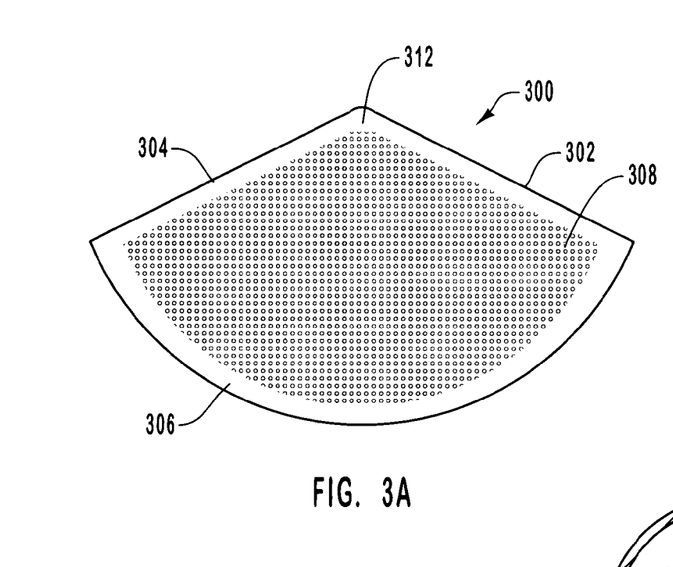
FIG. 3A illustrates a section of filter material for use in constructing a filter according to another embodiment of the present invention.
Figure 3B:
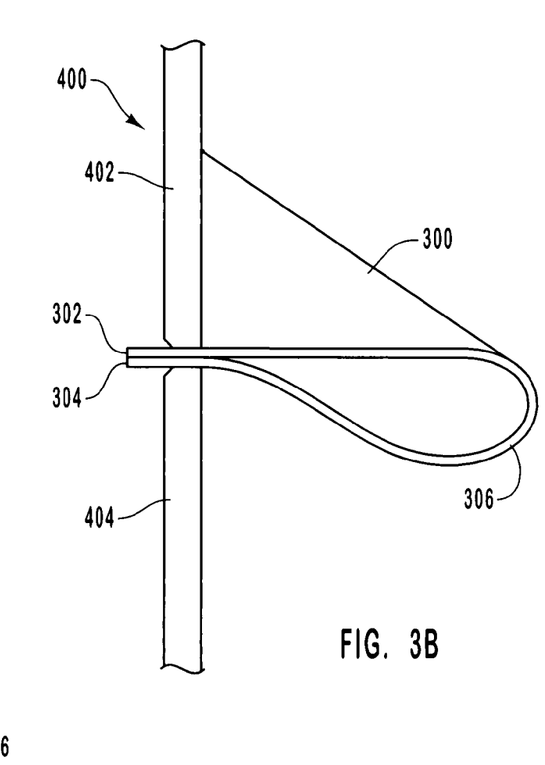
FIG. 3B illustrates a portion of a clamping assembly for assembling the section of filter material of FIG. 3A.
Figure 3C:
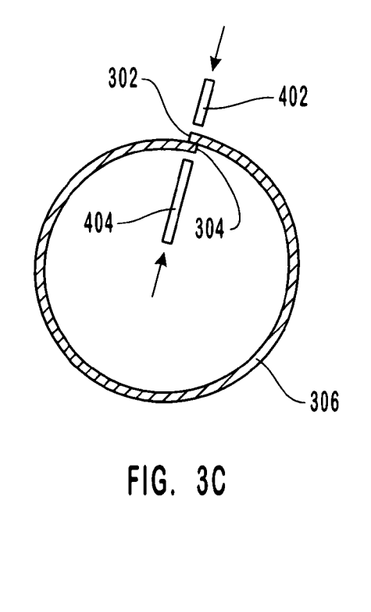
FIG. 3C illustrates a portion of another embodiment of a clamping assembly for assembling the section of filter material of FIG. 3A.

The filter 14 can be made from one or more pieces of filter material. In one embodiment, the filter 14 can be constructed from two pieces of filter material, as illustrated in FIGS. 2A-2C. In another embodiment, the filter 14 can be constructed from a single piece of filter material, as is illustrated in FIG. 3A-3C. While the pieces of filter material shown in FIG. 2A-2C and 3A-3C are shown as substantially flat, it will be appreciated that they can, in reality, have nonflat portions as commonly found in flexible materials.

With respect to FIGS. 2A through 2C, an embodiment is illustrated in which the filter 14 is constructed from two pieces of filter material identified as a first section 100A and a second section 100B. As shown in FIG. 2A, the first section 100A and the second section 100B are cut and configured to have substantially the same shape. The first section 100A and the second section 100B can be cut, under computer control, by an Eximer laser. Alternatively, the first section 100A and the second section 100B can be formed through use of a pattern. The pattern having the configuration or shape desired for the first section 100A and the second section 100B can be placed over a section of filter material, such as a section of polymer film. Once in place, a wide laser beam is passed over the pattern to burn away all of the filter material outside of the periphery of the pattern to leave behind the shaped piece. Alternatively, a solvent can be used to wash away material outside the edges of a pattern. However, care is taken so that the solvent does not penetrate within the perimeter of the pattern.

No matter the particular manner used to form the first section 100A and the second section 100B, an exemplary configuration of the first section 100A and the second section 100B is shown in FIG. 2A. Both sections 100A, 100B have a substantially tapered configuration. The following discussion will primarily describe an exemplary configuration of first section 100A, however, a similar discussion can be provided for the second section 100B.

As shown in FIG. 2B, the first section 100A has a substantially tapered configuration and includes a proximal end 102A and a distal end 104A, with the first section 100A generally tapering from the proximal end 102A to the distal end 104. It will be understood that the tapering of first section 100A provides the desired conical or tapered configuration of the filter 14. The proximal end 102A has a generally notched or serrated configuration with a plurality of protruding portions 106A which assist in connecting the filter 14 (FIG. 1) to other structures of the filter assembly 12 (FIG. 1). For example, as shown in FIG. 1, protruding portions 106A can be connected to the distal ends of or other portion of one or more struts 18.

Extending from the proximal end 102A toward the distal end 104A are edges 108A and 110A. These edges 108A and 110A are illustrated as being generally planar, however, the edges 108A and 110A can be curved or, alternatively, have protruding portions. The edges 108A and 110A have generally parallel first portions 112A and 114A and second portions 116A and 118A that are angularly orientated one to another. The inclusion of generally parallel first portions 112A and 114A aids with increasing the volume of filter 14 (FIG. 1) when first section 100A and second section 100B form filter 14. Additionally, the parallel first portions 112A and 114A form a constant cross-sectional portion of filter 14 that contacts the vessel wall during use of filter 14. Furthermore, parallel first portions 112A and 114A aid with creating a secure fit with struts 20 (FIG. 1) of filter basket 18 because the parallel portions 112A and 114A following the profile of filter basket 18.

The second portions 116A and 118A of first portion 112A and second portion 114A terminate at the distal end 104A, which can have a planar, curved, or pointed configuration. In other configurations, each edge 108A and 110A can taper from the proximal end 102A to the distal end 104A without the inclusion of generally parallel first portions 112A and 114A. Similarly, edges 108A and 110A can be substantially parallel from the proximal end 102A to the distal end 104A without the inclusion of generally angular second portions 116A and 118A. More generally, the first section 100A can have any desired polygonal configuration so long as it is capable of being formed into a sac-like configuration and attached to the filter assembly 12 (FIG. 1) so that it can collect emboli from flowing blood.

With continued reference to FIG. 2B, the first section 100A includes a porous region 120A. In the exemplary configuration, the porous region 120A is formed a distance from the outer periphery of the first section 100A. That is, a solid boundary 122A is formed around the porous region 120A. However, in other embodiments, the porous region 120A can be formed over the entire surface of first section 100A. The solid boundary 122A is configured such that when the first section 100A and second section 100B are placed adjacent to each other, the solid boundaries formed on the sections overlap and provide a surface that aids with bonding the first section 100A and the second section 100B together. As will be discussed further below, some or all of the solid portions 122A is eventually discarded leaving behind mostly the porous regions 120A.

The porous region 120A can be formed during manufacturing of the shapes of sections 120A. In one configuration, the pattern used to form the sections 100A and 100B can include a plurality of holes that match the location of the pores of the porous region 120A. As the wide beam laser passes over the pattern, the pores are formed in the filter material. In another configuration, a small diameter beam from a laser is used to form each individual pore. In still other configuration, solvents can be used to form the pores in porous region 120A. It will be understood that the pores need not be formed during the process of forming sections 100A and 100B. For instance, the filter material, such as a polymer film, can contain sufficiently sized pores such that additional pores do not need to be formed during the processes performed to form the first section 100A and the second section 100B.

The pores formed in the filter material of the filter 14 can have a variety of different configurations, such as but not limited to circular, oval, polygonal, combinations thereof or other configurations known to one skilled in the art in light of the teaching contained herein. In one configuration, the filter 14 includes uniformly sized pores having a diameter ranging from about 50 µm to about 200 µm. In another configuration, the diameter of the pores ranges from about 60 µm to about 180 µm. In still another configuration, the diameter of the pores ranges from about 75 µm to about 150 µm.

In another configuration, the filter 14 can include pores that are differently sized and configured. Consequently, a major or minor axis of each pore can have a variety of different sizes ranging from about 50 µm to about 200 µm, from about 60 µm to about 180 µm, or from about 75 µm to about 150 µm. Generally, the pore size can vary as needed, so long as the pores are sized so that the pores do not compromise blood flow through the filter 14, i.e., prevent blood flowing through the filter, and collect material that could potentially occlude smaller downstream vessels, potentially blocking blood flow to tissue or result in stroke or infarction.

In one configuration, the length $L_1$ of sections 100A is about 8 mm to about 20 mm. The length $L_2$ of the porous region 120A is about 7 mm to about 19 mm. The width of $W_1$ of the sections 100A is about 3 mm to about 14 mm. The width of $W_2$ of the porous region 120A is from about 25 mm to about 13 mm. These and any dimensions disclosed in the present invention are for purposes of illustration only are not to be limiting to the scope of the present invention.

The above discussion with regard to features and characteristics of the first section 100A also apply to the second section 100B. Sections 100A and 100B can have substantially the same size, or, alternatively, can differ in size.

Discussed thus far are the characteristics of the first section 100A and the second section 100B and the manner by which such are formed. Forming first section 100A and second section 100B is an initial step in the process of forming the filter 14 (FIG. 1). The pre-forming process can occur immediately before the process for joining, coupling or attaching two or more sections to create the filter 14 or occur at any time prior to the process of joining, coupling or attaching two or more sections to create the filter 14.

Referring back to FIG. 2A, to form the sack-like configuration of the filter 14, in one embodiment, a clamping assembly 200 is used. The clamping assembly 200 includes a first die portion 202A and a second die portion 202B. The die portions 202A, 202B provide first clamping surface 204A and second clamping surface 204B between which pieces of the filter material are placed and clamped during the filter construction process.

The clamping surfaces 204A, 204B of the first and second die portions 202A, 202B are preferably shaped substantially similar to the shape of the pieces of filter material. For example, in the embodiment above where the section 100A of filter material has two parallel portions 112, 114 and two angled portions 116, 118, the clamping surfaces 204A, 204B preferably have a similarly-shaped periphery each having two parallel portions and two angled portions. In one configuration, the periphery of the clamping surfaces 204A, 204B is smaller than the periphery of the sections 100A and 100B of the filter material. This allows portions of the filter material to be exposed outside the periphery of the die portions 202A, 202B to be accessible for bonding processes, which will be discussed further below.

The vertical sides of the die portions 202A, 202B are shown as substantially rectilinear such that, for example with regard to die portion 202A, the top surface has substantially the same shape as the clamping surface 204A. However, the vertical sides can be curved or tapered.

One function of the clamping assembly 200 is to hold the piece(s) of filter material during assembly of the sack-like configuration. Particularly, the clamping assembly 200 can be used to hold adjacent edges of the filter material together, whether from the same or different pieces of filter material. Thus, the clamping assembly 200 can be selectively positioned between an open and closed position. The die portions 202A, 202B include means for aligning the die portions when in the closed position. For example, the top die portion 202A includes alignment pins 206 while the bottom die portion 202B includes alignment apertures 208. When the clamping assembly 200 is closed, the alignment pins 206 are disposed in the alignment apertures 208 to align the die portions 202A, 202B. Other configurations for aligning die portions 202A, 202B can be applied. For instance, the location of the pins 206 and the apertures 208 can be reversed. Similarly, combinations of the pins 206 and the apertures 208 can be included on each of the die portions 202A and 202B. It can also be understood that other types and configurations of alignment structures can be used to align one die portion with another die portion.

Another function of the clamping assembly 200 is to form the boundaries for the bonding process. That is, the clamping assembly 200 allows the desired amount of filter material to be exposed to the bonding process, while protecting the rest of the filter material. As shown in FIG. 2C, the outer edge of the first clamping surface 204A and second clamping surface 204B has a slightly chamfered edge 210A, 210B. The length of the chamfer, X, is from about 75 μm (3 mils) to about 200 μm (8 mils). In one exemplary embodiment, the length of the chamfer X, is about 125 μm (5 mils). Thus, the clamping surfaces 204A, 204B provide an exposed portion of the sections 100A, 100B to be available for a bonding process. Although specific exemplary dimensions are provided herein, it will be understood by those skilled in the art that the chamfer can have any desired length based upon the amount of filter material used to bond the edges of the filter material to form the filter 14.

The combined chamfered edges 210A, 210B form a groove 212 which can hold bonding agent during the bonding process. In addition, a tool (e.g., a cotton swab, a bit, etc.) can be run along the length of the groove 212 to remove excess bonding agent and/or filter material. In this manner, the excess filter material can be removed.

The depth of chamfer, X, also forms the inner clamping edge, Y, beyond which, the bonding processes cannot substantially penetrate. For instance, when the bonding process includes using bonding agents to create the desired bond, the die portions 202A and 202B are clamped together with a sufficient force to prevent migration of the bonding agent substantially past the inner clamping edge Y. One or both clamping surfaces 204A, 204B can have a chamfered edge. Alternatively, neither clamping surface 204A, 204B can have a chamfered edge.

As discussed above, the periphery of the sections 100A, 100B of the filter material can be formed larger than the periphery of the clamping surfaces 204A, 204B such that a portion of the filter material extends beyond the periphery of the clamping surfaces 204A and 204B. For example, as shown in FIG. 2C, the sections 100A, 100B are exposed a distance Z past the clamping surfaces 204A and 204B. In one embodiment, the distance Z is about 500 μm (20 mils). This way, if the alignment of the first section 100A and second section 100B is off, it does not interfere with the formation of the filter. The particular distance Z can be greater than 500 μm or lesser than 500 μm depending upon the particular process performed. It is merely important that some portion of the filter material of sections 100A and 100B extend beyond the inner clamping edge Y.

Thus, it will be appreciated that the configuration of clamping assembly are not limited to the configuration of FIG. 2A, but can differ depending on the number of pieces of filter material which make up the filter, and the manner in which the piece(s) of filter material are bonded together. For example, clamping assembly 200 can have a blade configuration, discussed in more detail below.

In one configuration, the die portions 202A, 202B are constructed of a metal material. For example, the metal can be a stainless steel or tungsten. In another embodiment, the clamping surfaces 204A and 204B are constructed of a ceramic material. In any event, it is important that the material from which the clamping surfaces 204A and 204B are constructed is sufficient to withstand the selected bonding process and also provides enough clamping force between the two surfaces so as to prevent bonding agent or heat from penetrating too deep within the clamped area. In addition, it is desirable that the material of the clamping assembly 200 be reasonably corrosion resistant.

An exemplary process for bonding two sections of the filter material using the clamping assembly 200 is as follows. The first and second sections 100A, 100B are placed facing each other and laid horizontally on a first clamping surface 204A. A second clamping surface 204B is placed over the overlapped sections. The first section 100A overlaps the second section 100B such that at least a portion of the first edge 108A overlaps at least a portion of the second edge 108B and at least a portion of the second edge 110A overlaps at least a portion of the second edge 110B of the second section 104B. The first and second clamping surfaces 204A and 204B are closed using alignment pins 206 and alignment apertures 208 to align the clamping surfaces 204A and 204B.

In one configuration, because the first clamping surface and second clamping surface 204A, 204B are configured to have substantially the same shape as the first section 100A and second section 100B, when the clamping assembly closes, at least a portion of edges 108A, 108B and 110A, 110B are left exposed outside of the clamping assembly 200. However, portions of sections 100A, 100B can also be exposed without the clamping surfaces 204A and 204B being shaped the same as the sections 100A, 100B. As shown in FIG. 2C, the exposed portion of the edges 108A, 108B and 110A, 110B is available for a bonding process.

In one embodiment, the bonding process includes applying a bonding agent to the exposed portion of the overlapped edges 108, 110. The bonding agent could be a solvent, a polymer dissolved in a solvent, an adhesive, and the like. The bonding agent acts to bond the first section 100A to the second section 100B. In configurations using solvent as a bonding agent, the solvent also allows excess amounts of the filter material to be discarded so that a resulting seam (FIG. 1) formed between the first section 100A and second section 100B is extremely small. In one configuration, a low viscosity bonding agent is applied. The operator should ensure that the first clamping surface 204A and second clamping surface 204B are tightly engaged over the sections 100A, 100B so that the bonding agent does not penetrate beyond the inner clamping edge, Y. However, it is anticipated that a slight amount of the bonding agent may penetrate beyond the inner clamping edge, Y. In the event that this slight amount of bonding agent penetrates beyond the inner clamping edge, Y, it can contribute to the bonding formed between the first section 100A, and second section 100B.

In one embodiment, the solvent is dimethyl sulfoxide (DMSO). However, other solvents can also be suitable including, but not limited to, cyclohexanone, Stoddard solvent, acetone, or other solvents that can dissolve the filter material being used to form the filter. Suitable adhesives for use as bonding agents include, but are not limited to, cyanoacrylates and acrylic adhesives.

In another embodiment, the bonding process includes applying heat to the exposed portions of the edges 108, 110. Again, the heat drives away the excess filter material while providing a bond between the first section 100A and second section 100B. A combination of a bonding agent and heat can be used to bond the first section 100A to the second section 100B. In addition, the bonding process can include a laser welding process. The selected bonding process provides the seam 26 (FIG. 1) having the same or close to the same tensile strength as that of the filter material.

During or following application of the solvent, heat, or other bonding tool or process to the exposed filter material of the sections 100A and 100B, a tool (e.g., a cotton swab) can be applied to the groove 212 formed by the chamfered edges 210A, 210B. This tool removes excess bonding agent and/or the excess filter material to clean the seam 26.

With reference to FIGS. 3A through 3C, another exemplary configuration of the invention is illustrated in which a single piece of filter material is used to construct a filter. FIG. 3A shows a substantially tapered section 300 of filter material. The section 300 of filter material includes a first edge 302, second edge 304, and a third edge 306. The first edge 302 and second edge 304 are substantially linear while the third edge 306 has a curved shape. In addition, section 300 includes a porous region 308 that can have a similar configuration to the porous region 120. It will be appreciated that the section 300 can be constructed according to the methods described above with reference to sections 100A, and 100B. In the embodiment using a single section 300 of the filter material, the first edge 302 is configured to bond to the second edge 304. As such, a substantially sack-like filter can be formed having only a single seam 26 (FIG. 1) formed thereon.

With reference to FIG. 3B, the first edge 302 and second edge 304 are overlapped and placed between a clamping assembly 400. In this embodiment, the clamping assembly 400 includes a first blade 402 and a second blade 404. The first blade and second blade 402, 404 act to provide a high clamping force to the overlapping edges 302, 304. In addition, the blades can be chamfered similar to that described above with respect to clamping surfaces 204A, 204B. The blades 402, 404 allow at least a portion of edges 302, 304 of section 300 to be exposed to a bonding process while at the same time protecting the rest of the section from the bonding process. As such, a substantially conical sack-like filter is formed form a single piece of filter material. An additional step can be required to provide bonding agent or other bonding process at the tip 312 (FIG. 3A) in order to close the end of the filter.

Advantageously, a filter having only one seam 26 (FIG. 1) provides reduced number of steps for forming the filter. This can be desirable, especially in the embodiments where the filter material is extremely thin and difficult to handle.

With reference to FIG. 3C, another embodiment for placing the overlapping edges 302, 304 of section 300 is shown. In this embodiment, instead of facing surfaces of edges 302, 304 being placed adjacent each other, non-facing surfaces of the edges are placed adjacent each other. Bonding can then occur along one side of the blades 308, 310 to meld or melt the edges together.

It will be appreciated the blade clamping assembly 400 can be applied to the embodiment having two sections of the filter material. Vice versa, a clamping surface clamping assembly 200 can be applied to the single-piece embodiment to form the single seam. In another embodiment, the edges of the filter material can be manually held together and then a bonding process applied.

It will be understood that the blades and dies of the present invention can be moved through use of a variety of techniques and structures. For instance, the blades and dies can be mounting within racks or on tracks (not shown) that facilitate movement of the blades or dies during the bonding process. The blades and dies can, therefore, be moved under the influence of pneumatic or hydraulic rams, rack and gear systems, or other structures that can be used to move one die or blade toward another die or blade in a controlled and repeatable manner. Additionally, the blades and dies can be moved manually, automatically, or under the control of one or more electronic components that control the motion and position of the blades and dies.

The present invention can be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of constructing a filter for use in connection with an embolic protection device, the method comprising:
   forming a first section of a filter material by masking a larger section of a filter material according to a predetermined pattern and removing the excess filter material outside of the predetermined pattern with at least one of a laser beam and a solvent, the first section having a first edge and a second edge;
   contacting at least a portion of the first edge with at least a portion of the second edge;
   bonding together the at least a portion of the first edge with at least a portion of the second edge, such that the first section is formed into a sack-like shape.

2. The method of constructing a filter as recited in claim 1, wherein forming a first section of the filter material comprises laser cutting a larger piece of the filter material according to a predetermined pattern to form the first section.

3. The method of constructing a filter as recited in claim 1, wherein contacting at least a portion of the first edge and the second edge further comprises clamping at least a portion of the first edge and the second edge together using a clamping assembly.

4. The method of constructing a filter as recited in claim 3, wherein the clamping assembly comprises a first clamping surface and a second clamping surface.

5. The method of constructing a filter as recited in claim 4, wherein at least one of the first clamping surface and the second clamping surface includes a chamfered edge on the outer periphery thereof.

6. The method of constructing a filter as recited in claim 3, wherein the clamping assembly comprises a first blade and a second blade.

7. The method of constructing a filter as recited in claim 6, wherein at least one of the first blade and the second blade includes a chamfered edge.

8. The method of constructing a filter as recited in claim 1, wherein bonding together the at least a portion of the first edge with at least a portion of the second edge comprises contacting at least a portion of the first edge and at least a portion of the second edge with a bonding agent so as to form a bond between the first edge and the second edge.

9. The method of constructing a filter as recited in claim 1, wherein bonding together the at least a portion of the first edge with the at least a portion of the second edge comprises contacting at least a portion of the first edge and the second edge with sufficient heat so as to form a bond between the first edge and the second edge.

10. A method of constructing a filter for use in connection with an embolic protection device, the method comprising:
  forming a first section and a second section of a filter material by masking a larger section of a filter material according to a predetermined pattern and removing the excess filter material outside of the predetermined pattern with at least one of a laser beam and a solvent, the first section and the second section each having a first edge and a second edge;
  contacting at least a portion of the first edge of the first section and the first edge of the second section;
  contacting at least a portion of the second edge of the first section and the second edge of the second section;
  bonding together at least a portion of the first edges and the second edges, such that the first section and second section are formed into a sack-like shape.

11. The method of constructing a filter as recited in claim 10, wherein forming the first section and second section of filter material comprises laser cutting a larger piece of filter material according to a predetermined pattern.

12. The method of constructing a filter as recited in claim 10, wherein overlapping at least a portion of the first edge of the first section and the first edge of the second section further comprises clamping at least a portion of the first edge of the first section and the first edge of the second section together using a clamping assembly.

13. The method of constructing a filter as recited in claim 12, wherein the clamping assembly comprises a first clamping surface and a second clamping surface.

14. The method of constructing a filter as recited in claim 12, wherein at least one of the first clamping surface and the second clamping surface includes a chamfered edge on the outer periphery thereof.

15. The method of constructing a filter as recited in claim 12, wherein the clamping assembly comprises a first blade and a second blade.

16. The method of constructing a filter as recited in claim 15, wherein at least one of the first blade and the second blade includes a chamfered end.

17. The method of constructing a filter as recited in claim 10, wherein bonding together at least a portion of the overlapped first edges of the first section and second section comprises contacting at least a portion of the overlapped first edges with a bonding agent so as to form a bond between the first edges.

18. The method of constructing a filter as recited in claim 10, wherein bonding together at least a portion of the overlapped first edges of the first section and second section comprises contacting at least a portion of the overlapped first edges with sufficient heat so as to form a bond between the first edges.

* * * * *